United States Patent [19]
Vinci et al.

[11] Patent Number: 5,382,678
[45] Date of Patent: Jan. 17, 1995

[54] BATCH PROCESS FOR FATTY ACID ALKALINE EARTH METAL SALT PRODUCTION

[75] Inventors: Alfredo Vinci, Dayton; Kenneth R. Cummings, Skillman; M. Stephen Lajoie, Basking Ridge, all of N.J.

[73] Assignee: Church & Dwight Co., Inc., Princeton, N.J.

[21] Appl. No.: 285,432

[22] Filed: Aug. 4, 1994

Related U.S. Application Data

[63] Continuation of Ser. No. 77,090, Jun. 16, 1993, abandoned.

[51] Int. Cl.$^6$ .............................................. A23K 1/00
[52] U.S. Cl. ............................ 554/156; 426/72; 426/74; 426/656; 426/658; 426/807
[58] Field of Search ............... 554/156; 426/72, 74, 426/656, 658, 807

[56] References Cited
U.S. PATENT DOCUMENTS
5,215,768  6/1993  Vinci et al. .......................... 46/74

*Primary Examiner*—José G. Dees
*Assistant Examiner*—Deborah D. Carr
*Attorney, Agent, or Firm*—Charles B. Barris

[57] ABSTRACT

This invention provides an improved process for the production of a fatty acid alkaline earth metal salt product which have little or no content or glyceride ingredient. An essential feature of the process is the pre-blending of glyceride-containing fatty acid feedstock and basic alkaline earth metal compound, before mixing with water and heating the mixture to initiate salt-forming and glyceride-hydrolyzing reactions. The fatty acid alkaline earth metal salt product can be recovered in the form of tackless free-flowing dust-free granules.

7 Claims, No Drawings

BATCH PROCESS FOR FATTY ACID ALKALINE EARTH METAL SALT PRODUCTION

This application is a continuation of application Ser. No. 08/077,090, filed Jun. 16, 1993, now abandoned.

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is an excellent energy source, and it is known that if the proportion of fat in cattle food is increased, lactating dairy cattle produce high milk yields without draining their reserves of body fat and without diminishing the proportion of milk fat in the milk produced.

However, it has been found that if the proportion of fat in the diet of cattle exceeds about 3–5 of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, such later fiber digestion produces a blend of different fatty acids than that which is produced by the digestion in the rumen, and the different blend of fatty acids is less suited to the cow's metabolism.

It is known also that fatty acid esters and free fatty acids can physically coat fibrous or cellulosic material in the rumen and inhibit fermentation of the material by the bacteria. This has an adverse effect on the total digestibility of the diet, and can result in a reduced yield of milk and butter-fat.

There has been a continuing need for new dietary supplements for animal feedstuff which can be fed to ruminant animals without interfering with nutrient metabolism by rumen microorganisms.

U.S. Pat. Nos. 4,642,317; 4,826,694; 4,853,233; and 4,909,138 describe the incorporation of insoluble fatty acid salts in ruminant feed as a means of increasing the fatty acid content without deleteriously affecting the ruminant digestion cycle. A feed additive such as fatty acid calcium salt functions as a rumen bypass product, and is subsequently metabolized in the abomasum or small intestine of the ruminant.

A further consideration is the provision of a fatty acid alkaline earth metal salt most conveniently in the form of friable solids. Less desirable forms of fatty acid salts are dusty powders or tacky solids, which are less suited than free-flowing dust-free granules for utility as a dietary supplement in animal feed. Tacky solids can coat cellulosic materials and inhibit fermentation of the cellulosics by bacteria in the rumen.

Accordingly, it is an object of this invention to provide a fatty acid alkaline earth metal salt which is the form of tackless friable solids.

It is another object of this invention to provide an improved process for converting a glyceride-containing fatty acid feedstock into a fatty acid alkaline earth metal salt which contains little or no fatty acid glyceride, and which can function as a rumen bypass animal feed supplement and promote a beneficial increase in dietary fat consumption by ruminants.

Other objects and advantages of the present invention shall become apparent from the accompanying description and examples.

DESCRIPTION OF THE INVENTION

One or more objects of the present invention are accomplished by the provision of a process for the preparation of a fatty acid salt product which comprises (1) forming an admixture of reactive ingredients comprising (a) $C_{12}$–$C_{22}$ fatty acid, having about 5–40 weight percent of the $C_{12}$–$C_{22}$ fatty acid content in glyceride form, and (b) between about 1–1.8 equivalents of basic alkaline earth metal compound per equivalent of $C_{12}$–$C_{22}$ fatty acid; (2) adding between about 10–120 weight percent of water to the admixture, based on the admixture weight, to form an aqueous suspension medium; (3) heating the aqueous suspension medium to a temperature in the range between about 40°–130° C.; (4) maintaining the reaction temperature for a time period sufficient to complete the fatty acid salt-forming reaction, and to hydrolyze glyceride to fatty acid salt and glycerol; and (5) recovering the fatty acid salt product as friable solids which have a glyceride content of less than about 5 weight percent on a dry basis.

An essential aspect of the invention process is the pre-blending of glyceride-containing fatty acid feedstock and basic alkaline earth metal compound in step (1), before mixing the pre-blend with water in step (2), and heating the mixture in step (3) to initiate salt-forming and glyceride-hydrolyzing reactions. The fatty acid alkaline earth metal salt product is recovered in the form of tackless free-flowing granules.

If the fatty acid feedstock is pre-blended with the aqueous medium, and the pre-blend subsequently is admixed with the basic alkaline earth metal compound as described in U.S. Pat. No. 3,051,571, then the final product is obtained in the form of a dusty powder. If the basic alkaline earth metal compound is pre-dispersed in the aqueous medium, and the dispersion subsequently is admixed with the fatty acid feedstock, then the final product is obtained in the form of tacky solids.

The processing parameters of the present invention process are adapted to provide a preferred tackless free-flowing granulated form of the fatty acid alkaline earth metal salt product, which is suitable for direct use as an animal feed supplement.

In step (3) of the invention process, the temperature of the aqueous suspension medium is increased to initiate the salt-forming and glyceride-hydrolyzing reactions. Optionally, the step (1) admixture can be heated before it is combined with the aqueous medium in step (2). Also, the basic alkaline earth metal compound hydration reaction is exothermic and generates heat in the aqueous suspension medium.

The amount of aqueous medium employed is sufficient to provide an available volume of aqueous solution for hydrolysis of the glyceride content to fatty acid and glycerol under alkaline conditions. If an insufficient quantity of water is introduced in the invention process reaction medium, then little or no hydrolysis of the glyceride content occurs. The reaction temperature and reaction time are other factors which influence the extent of glyceride hydrolysis during the salt-forming stage of the invention process.

The elevated temperature conditions in step (4) are maintained for a time period between about 0.2–8 hours, which is sufficient to complete the fatty acid salt-forming reaction, and to hydrolyze glyceride to fatty acid salt and glycerol.

As the fatty acid salt-forming reaction tends to completion, the pH of the aqueous suspension medium increases and the glyceride hydrolysis reaction proceeds more readily. The present invention process can produce a fatty acid alkaline earth metal salt product which has a glyceride content of less than about 0.5 weight percent. A present invention fatty acid salt product can be essentially free of glyceride content.

The $C_{12}$–$C_{22}$ fatty acid ingredient of the process salt-forming reaction medium consists of one or more saturated or unsaturated carboxylic acids derived from animal fat and vegetable oil sources such as beef and mutton tallow, lard, cottonseed oil, palm oil, and the like.

Palm fatty acid distillate is a commercial product produced by distilling the fatty acids present in natural palm oil. A distillate product typically has the following weight percent content:

| | |
|---|---|
| Free fatty acids | 70–90 |
| Triglycerides | 10–30 |
| Moisture, insolubles and unsaponifiables | <5 |

The fatty acids in the free fatty acids and the triglycerides normally consist of the following weight percent:

| | |
|---|---|
| Palmitic acid | 38–50 |
| Oleic acid | 35–40 |
| Linoleic acid | 5–10 |
| Stearic acid | 3–6 |
| Lauric acid | 1–6 |

Beef tallow acids are available commercially as a byproduct obtained by alkaline extraction of waste beef fat and subsequent acidification, and normally contain the following weight percent of fatty constituents:

| | |
|---|---|
| Free fatty acids | 60–90 |
| Triglycerides | 10–40 |
| Water | <1 |
| Unsaponifiables | <3 |

The fatty acids in the free fatty acids and in the triglycerides normally have the following weight percent content:

| | |
|---|---|
| Palmitic acid | 22–28 |
| Oleic acid | 38–44 |
| Linoleic acid | 3–6 |
| Stearic acid | 18–24 |

The term "glyceride" as employed herein includes $C_{12}$–$C_{22}$ fatty acid monoglycerides, diglycerides and triglycerides, and any mixture thereof.

Because $C_{12}$–$C_{22}$ fatty acids and glycerides are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid bulk ingredient.

Illustrative of preferred additives are butylated hydroxytoluene, tocopherol and ethoxyquin antioxidant, and citric acid and ethylenediamine tetraacetate chelating agents. The chelating agent is added in an edible solvent such as propylene glycol to facilitate blending into the fatty acid.

The alkaline earth metal compound ingredient of the process is at least one member selected from the group consisting of basic calcium and magnesium compounds, such as oxides, carbonates, phosphates, hydroxides, and the like. The alkaline earth metal component preferably has a particle size which passes a 100 mesh U.S. standard screen.

A biologically active constituent can be included as an optional ingredient in the invention process. The biologically active constituent can be selected from a broad variety of nutrients and medicaments, either as a single component or as a mixture of components, which are illustrated by the following listing of active molecular species:

1. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

2. aminoacid ingredients either singly or in combination which include arginine, histidine, isoleucine, leucine, lysine, methionine, phenylalanine, threonine, tryptophan, valine, tyrosine ethyl HCl, alanine, aspartic acid, glutamic acid, sodium glutamate, potassium glutamate, glycine, proline, serine, cysteine ethyl HCl, and the like, and analogs and salts thereof.

3. vitamin ingredients either singly or in combination which include thiamine HCl, riboflavin, pyridoxine HCl, niacin, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

4. protein ingredients as obtained from sources such as dried blood or meat meal, cottonseed meal, soybean meal, rapeseed meal, dehydrated alfalfa, dried and sterilized animal and poultry manure, fish meal, fish and poultry protein isolates, liquid or powdered egg, fish solubles, cell cream, and the like.

It is another advantage of the present invention process that the protein ingredient is partially or completely denatured under the processing conditions of temperature and alkaline pH. The denatured protein is water-insoluble, and exhibits rumen bypass properties when it is a constituent of a ruminant feedstuff.

5. medicament ingredients either singly or in combination which include promazine hydrochloride, chloromadionate acetate, chlorotetracycline, sulfamethazine, monensin, sodium monensin, poloxaline, and the like. Oxytetracycline is a preferred antibiotic for cattle prophylaxis.

6. antioxidants as illustrated by butylated hydroxyanisole, butylated hydroxytoluene, tertiary-butylhydroquinone, tocopherols, propyl gallate, and ethoxyquin; and suitable preservatives include sodium sorbate, potassium sorbate, sodium benzoate, propionic acid, α-hydroxybutyric acid, and the like.

7. suspension stabilizing agents which preferably are selected from nonionic surfactants, hydrocolloids and cellulose ethers. These types of chemical agents are illustrated by polyethylene oxide condensates of phenols, $C_8$–$C_{22}$ alcohols and amines; ethylene oxide reaction products with fatty acid partial esters of hexitans; alkylarylpolyoxyethylene glycol phosphate esters; gum arabic; carob bean gum; guar gum; tragacanth gum; ammonium, sodium, potassium and calcium alginates; glycol alginates; xanthan gum; potato agar; alkylcellulose; hydroxyalkylcellulose; carboxyalkylcellulose; lecithin; and the like.

The biologically active ingredient is present in a quantity between about 0.05–20 weight percent, based on the weight of $C_{12}$–$C_{22}$ fatty acid bulk ingredient.

The following Example is further illustrative of the present invention. The components and specific ingredients are presented as being typical, and various modifications can be derived in view of the foregoing disclosure within the scope of the invention.

EXAMPLES

This Example illustrates the production of fatty acid calcium salt in accordance with the present invention process.

A batch reaction is conducted for the preparation of palm oil distillate calcium salt. The palm oil distillate has the following composition:

| | |
|---|---|
| Lauric acid | 2.3% |
| Palmitic acid | 49.9% |
| Stearic acid | 5.4% |
| Oleic acid | 35.0% |
| Linoleic acid | 7.4% |

About 15 weight percent of the fatty acid is in the form of glyceride ester.

A.

Calcium oxide (2366 g, 42.25M) and hot palm oil distillate (80° C.) (17 kg, 65M) are blended in a kettle reactor with stirring. Warm water (6 liters) is added to the reactor contents with stirring, and the aqueous suspension medium is heated to 90° C. After a short induction period, an exothermic reaction commences and the temperature of the reaction medium increases to about 110° C. The reaction medium temperature is maintained at about 110° C. for two hours.

The resultant fluid product medium is poured into a broad-surface pan. After cooling and drying, the fatty acid calcium salt product is obtained in the form of friable solids. The fatty acid calcium salt product is passed through a sizing machine and a sifter. The final fatty acid calcium salt product is in the form of tackless free-flowing granules which are essentially free of glyceride content.

B.

The above-describe procedure is repeated, except that the fatty acid and aqueous medium are pre-mixed, and subsequently the calcium oxide ingredient is added.

The final fatty acid calcium salt product is obtained as a dry powder, which has a content of about 3 weight percent of glyceride.

C.

The above-described procedure is repeated, except that the aqueous medium and calcium oxide are pre-blended, and subsequently the fatty acid ingredient is added.

The final fatty acid calcium salt product is obtained as an inhomogeneous, tacky mass, which has a content of occluded, unreacted fatty acid and glyceride ingredients.

What is claimed is:

1. A batch process for the preparation of a fatty acid salt product with steps which consist of (1) forming an admixture of reactive ingredients consisting essentially of (a) $C_{12}$–$C_{22}$ fatty acid, having about 5–40 weight percent of the $C_{12}$–$C_{22}$ fatty acid content in glyceride form, and (b) between about 1–1.8 equivalents of basic alkaline earth metal compound per equivalent of $C_{12}$–$C_{22}$ fatty acid; (2) adding between about 10–120 weight percent of water to the admixture, based on the admixture weight, to form an aqueous suspension medium; (3) heating the aqueous suspension medium to a temperature in the range between about 40°–130° C.; (4) maintaining the reaction temperature for a time period between about 0.2–8 hours sufficient to complete the fatty acid salt-forming reaction, and to hydrolyze glyceride to fatty acid salt and glycerol; and (5) recovering the fatty acid salt product as tackless free-flowing granules which have a glyceride content of less than about 5 weight percent.

2. A process in accordance with claim 1 wherein the fatty acid ingredient is a mixture comprising 0–10 percent lauric acid, 0–60 percent palmitic acid, 0–10 percent stearic acid, 0–60 percent oleic acid, and 0–10 percent linoleic acid.

3. A process in accordance with claim 1 wherein the fatty acid ingredient is palm fatty acid distillate with a glyceride content.

4. A process in accordance with claim 1 wherein the alkaline earth metal ingredient is a basic calcium compound or magnesium compound or a mixture thereof.

5. A process in accordance with claim 1 wherein a biologically active ingredient is added as an optional ingredient to the admixture in step (1) or step (2).

6. A process in accordance with claim 1 wherein between about 0.05–20 weight percent of aminoacid or protein, based on the weight of $C_{12}$–$C_{22}$ fatty acid bulk ingredient, is added as an optional ingredient to the admixture in step (1) or step (2).

7. A process in accordance with claim 1 wherein the recovered fatty acid salt product in step (5) has a glyceride content less than about 0.5 weight percent.

* * * * *